(12) United States Patent
Cao et al.

(10) Patent No.: US 7,872,465 B2
(45) Date of Patent: Jan. 18, 2011

(54) APPARATUS AND METHODS FOR EVALUATING MATERIAL VOLATILITY

(75) Inventors: Tuan Quang Cao, Kirkland, WA (US); Thomas D. Hayward, Tacoma, WA (US); Benjamin E. Koltenbah, Federal Way, WA (US); George A. Perry, Federal Way, WA (US); James Robert Beymer, Maple Valley, WA (US)

(73) Assignee: The Boeing Company, Chicago, IL (US)

( * ) Notice: Subject to any disclaimer, the term of this patent is extended or adjusted under 35 U.S.C. 154(b) by 167 days.

(21) Appl. No.: 11/173,876

(22) Filed: Jun. 30, 2005

(65) Prior Publication Data

US 2007/0000331 A1 Jan. 4, 2007

(51) Int. Cl.
*G01N 27/00* (2006.01)
*G01N 3/30* (2006.01)
(52) U.S. Cl. .................................. 324/71.1; 73/12.08
(58) Field of Classification Search ............... 324/72, 324/71.1, 460, 464, 456; 73/12.08
See application file for complete search history.

(56) References Cited

U.S. PATENT DOCUMENTS

| | | | | |
|---|---|---|---|---|
| 3,840,809 A * | 10/1974 | Yun | ............................ | 324/765 |
| 3,939,693 A * | 2/1976 | Dumont | ...................... | 73/19.05 |
| 4,755,904 A * | 7/1988 | Brick | .......................... | 361/117 |
| 4,998,076 A | 3/1991 | Von Bokern | | |
| 5,103,193 A | 4/1992 | Von Bokern | | |
| 5,285,251 A * | 2/1994 | Pilloud et al. | ................ | 356/313 |
| 5,503,001 A * | 4/1996 | Wong | ............................ | 73/38 |
| 5,777,479 A | 7/1998 | Kuhlman | | |
| 5,949,343 A * | 9/1999 | Sesekura et al. | ............. | 340/683 |
| 6,560,314 B2 * | 5/2003 | Poulsen | ....................... | 378/143 |
| 6,662,631 B2 * | 12/2003 | Baklanov et al. | ............... | 73/38 |
| 2003/0027471 A1 * | 2/2003 | Shimazaki et al. | ............ | 442/59 |
| 2007/0164206 A1 * | 7/2007 | Ishiuchi | ...................... | 250/282 |

* cited by examiner

*Primary Examiner*—Jeff Natalini
(74) *Attorney, Agent, or Firm*—Harness, Dickey & Pierce, P.L.C.

(57) ABSTRACT

A method of evaluating material volatility characteristics. A pulse of current flux is delivered through a material sample to simulate a lightning strike. A pressure produced by the sample during the pulse is measured. The measured pressure is used to measure volatility of the material. An apparatus for evaluating the volatility of materials includes a pulse power supply and a test cell through which a pulse is delivered and in which pressure produced by a sample during the pulse is measured. This apparatus and method can reduce the costs of material selection and can shorten development time for new products.

10 Claims, 7 Drawing Sheets

APPARATUS AND METHODS FOR EVALUATING MATERIAL VOLATILITY

FIELD OF THE INVENTION

The present invention relates to materials testing and more particularly (but not exclusively) to the use of flash heating to evaluate the volatility and/or ablation characteristics of materials.

BACKGROUND OF THE INVENTION

Carbon fiber composites offer high strength-to-weight ratios for aircraft design and are increasingly used on modern aircraft. It is desirable to understand the behavior of resins in composites when subjected to lightning strikes to better select materials, determine lightning thresholds, and design protection schemes for aircraft. The use of traditional lightning tests for evaluating the performance of resins can be time-consuming, and may be cost-prohibitive for effectively screening the wide variety of composite resins available for use.

SUMMARY OF THE INVENTION

The present invention, in one implementation, is directed to a method of evaluating material volatility characteristics. A pulse of current flux is delivered through a material sample to simulate a lightning strike. A pressure produced by the sample during the pulse is measured. The measured pressure is used to measure volatility of the material.

In another implementation, the invention is directed to a test apparatus including a pulse power supply configured to deliver a pulse of current flux to a test subject to simulate a lightning strike. The pulse power supply includes an insulated gate bipolar transistor (IGBT) having a collector and emitter through which the current flux is delivered to the subject, and control electronics that control a gate of the IGBT to control the pulse.

In yet another implementation, the invention is directed to an apparatus for evaluating the volatility of materials. The apparatus includes a pulse power supply and a test cell having a plurality of electrodes configured to deliver a pulse from the pulse power supply through a material sample. A pressure transducer is configured to sense a pressure difference within the test cell due to the pulse. A data acquisition system is configured to receive a signal from the pressure transducer representative of the pressure difference, and evaluate the material sample based on the pressure difference and a specific energy deposited in the material sample due to the pulse.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF EMBODIMENTS

The following description of various embodiments is merely exemplary in nature and is in no way intended to limit the invention, its application, or uses. Corresponding reference numbers indicate corresponding (although not necessarily identical) parts throughout the several views of the drawings. Although various configurations of the invention are described as including particular hardware and/or software components, the invention is not so limited. Configurations of the invention also are contemplated which include alternative and/or additional hardware and/or software components.

Generally, when a material sample is flash-heated to a pyrolytic temperature similar in duration and current density to that of a lightning strike, a behavior of the sample can be determined by measuring the pressure of evolved gases during the flash-heating. Sample behavior can be directly related to the quantity of volatizeable compounds in the sample and the vapor-pressures of such compounds at the temperatures of interest.

In some implementations of the invention, resistive heating is used to rapidly heat materials to pyrolytic temperatures. For example, a pre-designated finite-energy pulse may be delivered to a test sample to burn off organic materials in the sample. An evolved quantity of volatiles is gauged by a maximum measured pressure. The maximum measured pressure can be used to evaluate the lightning tolerance performance of the materials.

Figure 1:
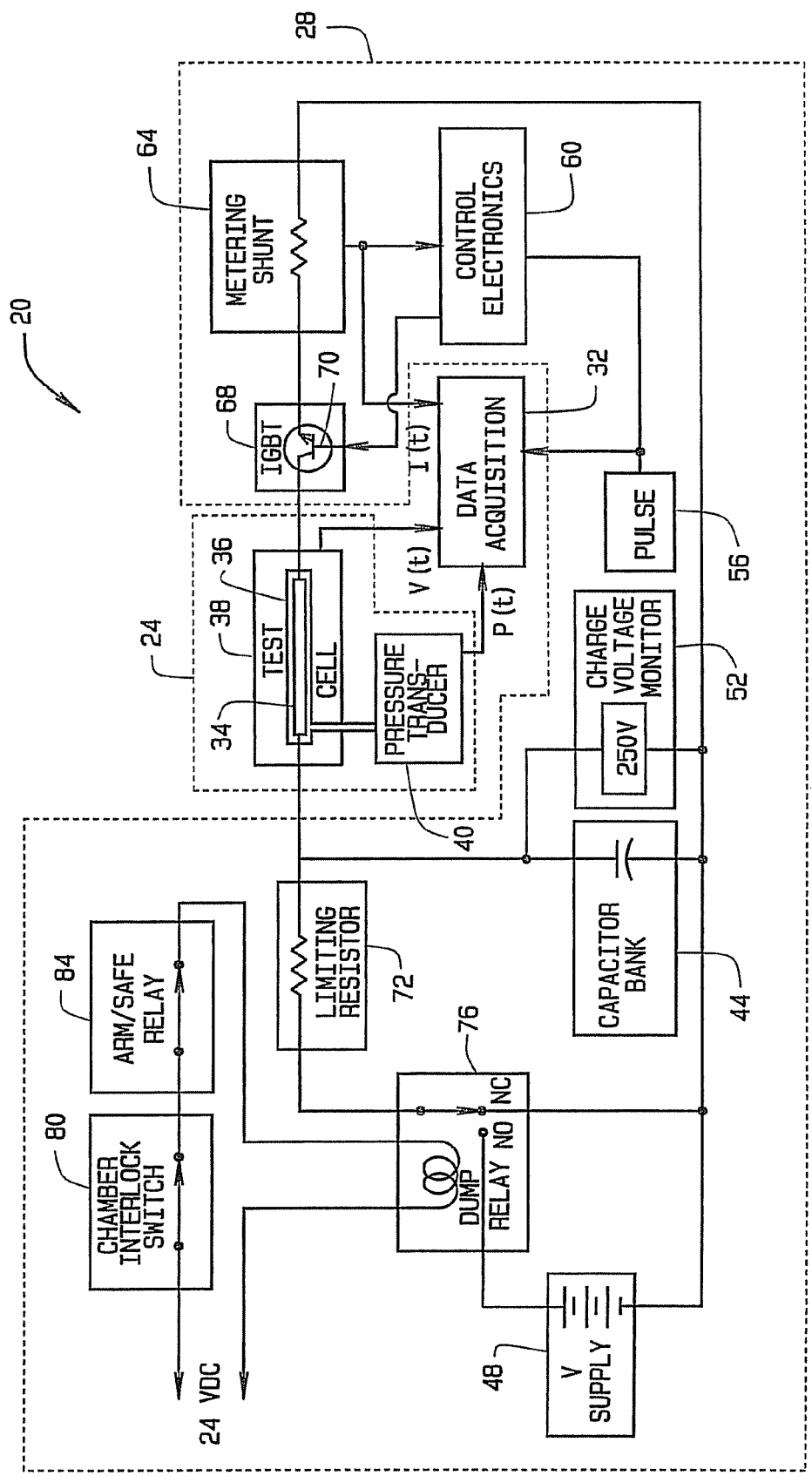
FIG. 1 is a block diagram of an apparatus for testing the volatility of materials in accordance with one implementation of the invention.

One configuration of an apparatus for testing the volatility of materials is indicated generally by reference number 20 in FIG. 1. The apparatus 20 includes a test cell assembly 24, a pulsed power supply system 28, and a data acquisition system 32. The power supply system 28 is configured to produce a pre-programmed current pulse through a sample 34 in a test chamber 36 of a test cell 38. In one configuration the chamber 36 has a small dead volume (e.g., less than 0.03 cubic inches) and is air-tight. A pressure transducer 40 is configured to sense pressure changes caused by heating of materials in the test chamber 36 and to send a signal representative of a pressure change to the data acquisition system 32.

The pulsed power supply system 28 includes a capacitor bank 44, a high-voltage supply 48, a charge voltage monitor 52, a pulse generator 56, pulse control electronics 60, a metering shunt 64, an insulated gate bipolar transistor (IGBT) 68, a limiting resistor 72, a dump relay 76, a chamber interlock switch 80, and an arm/safe relay 84. As further described below, the data acquisition system 32 utilizes a pressure signal from the pressure transducer 40, a voltage signal from the test cell 38, a current signal from the shunt resistor(s) 64, and a pulse signal from the pulse generator 56.

The capacitor bank 44 is configured to hold energy that discharges through the sample. The pulse control electronics 60 control an amount of electrical energy to be discharged. The pulse control electronics 60 utilize the IGBT 68 to control a pulse width and current level supplied to electrodes (not shown in FIG. 1) of the test cell assembly 24. It should be noted that the IGBT 68 is used as a current regulator and not in a conventional switch mode. The IGBT 68 is used in a short pulse mode, as a firing mechanism to deliver controlled pulse energy with high current flux and a short duration for a volatility test as further described below. The control electronics 60 are configured to sense current from the IGBT 68 and control a gate 70 of the IGBT to control an amplitude and width of the current pulse. The IGBT 68 may be rated, for example, at 2000 A and 1000V. An exemplary IGBT is P/N DIM800FSM12-A0000, rated at 800 A, 1200V, and 6940 watts. Voltage feedback from the current sense resistor 64 is used to control a square pulse waveform from the pulse generator 56. The pressure transducer 40 may be a piezoelectric transducer, for example, a model 112A22 transducer from PCB Piezotronics, Inc., Depew, N.Y., and may be used with a PCB Piezotronics model 482A21 signal conditioner.

The data acquisition system 32 includes a data acquisition and control computer with which the pulsed power supply system 28 interfaces, e.g., through a data acquisition board located in a PCI expansion slot on the computer motherboard. The data acquisition board may be obtained, for example, from National Instruments Corporation of Austin, Tex.

The apparatus 20 collects the time, voltage and current of the pulse passing through test specimens during a test, and also collects pressure signals from the transducer 40. The sampling rate of the apparatus 20 is, for example, 100 kHz per channel. The apparatus software integrates the voltage and current signal in real time to yield a total electrical energy that passes through the test specimen. Test results are reported on the user interface screen.

Figure 2:
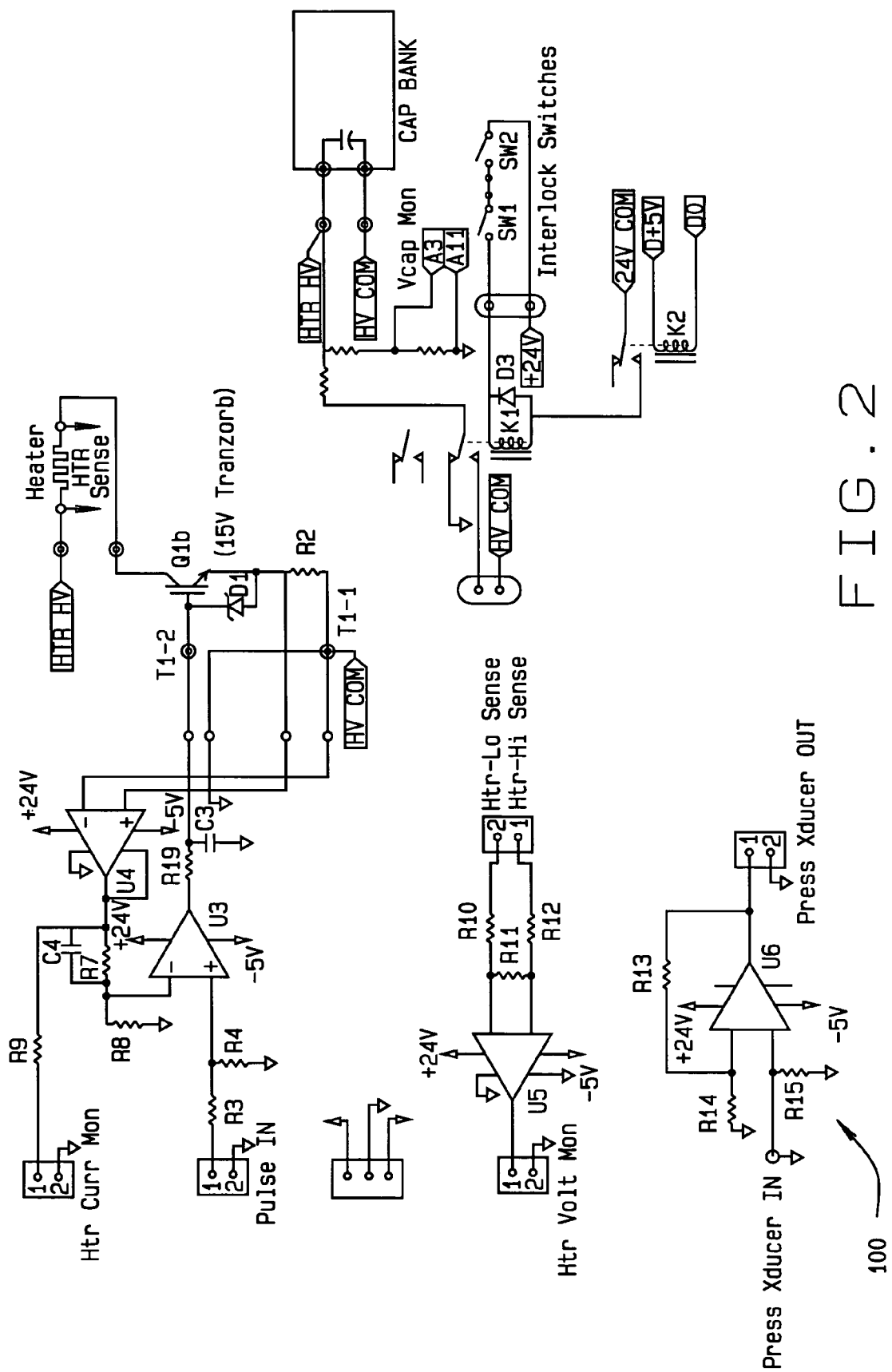
FIG. 2 is a circuit diagram of a pulse control circuit in accordance with one implementation of the invention.

Exemplary operating characteristics of the power supply system 28 are shown in Table 1. One configuration of a pulse control circuit is indicated generally in FIG. 2 by reference number 100. Exemplary values for pulse control circuit components shown in FIG. 2 are shown in Table 2.

TABLE 1

Pulsed power supply system exemplary operating characteristics

| | |
|---|---|
| Output current | Adjustable in IA steps from 0 to 1000 A with a compliance voltage (capacitor bank charge voltage) of up to 430 V. The output current capability decreases as compliance voltage is increased. |
| Output Current Pulse Width | Adjustable from 0.1 ms to 1000 ms in 0.1 ms increments. The output current capability decreases with increasing pulse width. |
| Output Current Pulse Rise/Fall Slewing Rates | >6 A/μs (<100 μs for 600 A pulse). |
| Typical Operating Conditions | Up to 600 A at 100 V for 5 ms, Up to 200 A at 400 V for 5 ms |
| Heater Voltage Monitoring Range (differential) | 0 V to 400 V with a common mode range of > 600 V |
| Heater Current Monitor range | 0 A to > 1000 A |

TABLE 1-continued

Pulsed power supply system exemplary operating characteristics

| | |
|---|---|
| Pressure Monitor range | 0 psi to 20 psi. |
| Pressure Monitor response time | <2 μs. (sensor alone, chamber volume affects this) |

TABLE 2

Control Circuit Exemplary Values

| | | | |
|---|---|---|---|
| R2 - .01Ω | R3 - 2.67 kΩ | R4 - 361 Ω | R7 - 900 Ω |
| R8 - 162 Ω | R9 - 4.99 kΩ | R10 - 5.11 kΩ | R11 - 348 Ω |
| R12 - 5.11 kΩ | R13 - 36.5 kΩ | R14 - 9.09 kΩ | R15 - 49.9 kΩ |
| R16 - 48Ω, 100 W | R17 - 99 kΩ | R18 - 1 kΩ | R19 - 10 Ω |
| C3 - 2 uF | C4 - 3.9 nF | U3 - LM7171 | U4 - AMP03 |
| U5 - AD629 | U6 - OP27 | B1 - 15 V Tranzorb | |
| Cap Bank - 60 mF | (20 × 3000 uF) | | |

Figure 3:
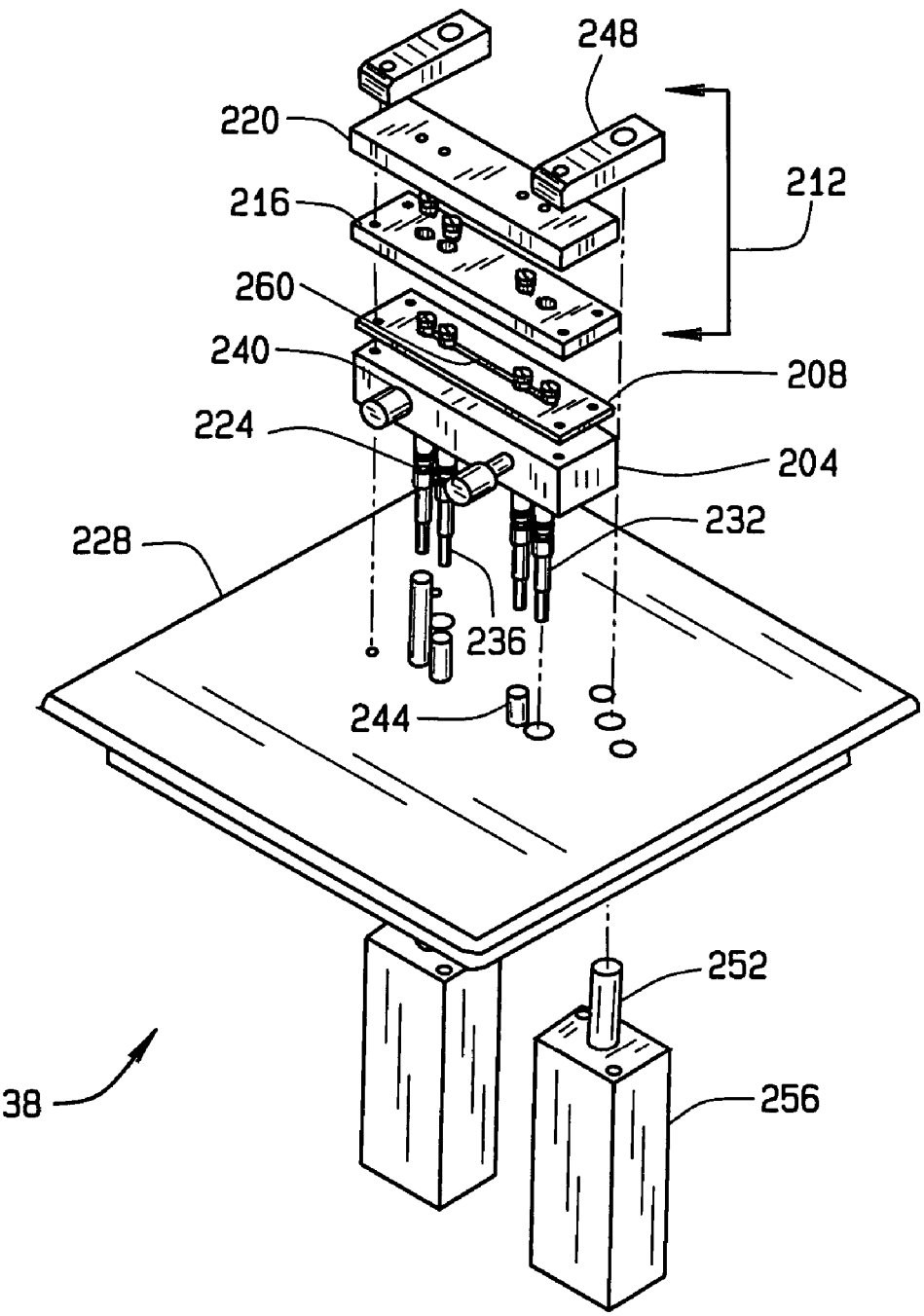
FIG. 3 is an exploded perspective view of a test cell in accordance with one implementation of the invention.

An exploded perspective view of one embodiment of the test cell 38 is shown in FIG. 3. The test cell 38 includes an isolator block 204 and a chamber spacer 208. A top enclosure assembly 212 includes a cap guide plate 216 and a clamp plate 220. The isolator block 204 includes a plurality of feedthrough holes (not visible in FIG. 3) through which a plurality of electrodes 224, e.g., four electrodes, penetrate to interface with the pulsed power supply system 28. The electrodes 224 also pass through a base plate 228 for connection with the power supply system 28. The electrodes 224 provide current and voltage feedback to the pulse power supply system 28. The electrodes 224 include an outer pair of current electrodes 232 and an inner pair of voltage sense electrodes 236. An exemplary distance between the voltage electrodes 236 is about 1.75 inches.

The isolator block 204 also includes ports 240 in which valves, e.g., refrigeration Schrader valves 330, may be removably installed for pressure sensing and/or purging as further described below. The isolator block 204 may be fabricated, for example, of Delrin® (polyoxymethylene) material. Two capillary channels (not shown) between the voltage sense electrodes 236 and the current electrodes 232 connect with the two ports 240.

The base plate 228 includes a plurality of (in the present configuration, four) four banana jacks 244 into which the electrodes 224 can be plugged. The base plate 228 may be equipped with two pneumatic clamps 248 to hold the test cell 38 securely on the base plate 228 and also keep the test cell 38 airtight during a pulse current test. The clamps 248 may be attached to a pair of pistons 252 extending through the base plate 228 from pneumatic clamp cylinders 256.

The test cell 38 typically has a very small dead volume to allow a small amount of volatile generated during a pulsed current test to develop a measurable pressure. The chamber spacer 208 has a slot 260 that forms the sealed sample chamber 36 when it is assembled with the isolator block 204 and the top enclosure assembly 212. The dead volume of the sample chamber 36 is, for example, less than 0.03 cubic inches, excluding the dead volume of fittings included therein. The test cell 38 accommodates a material sample that does not touch the ends of the cell, e.g., a sample about 2.94 inches long. The chamber spacer 208 may be made of fiberglass/epoxy composite.

Figure 4:
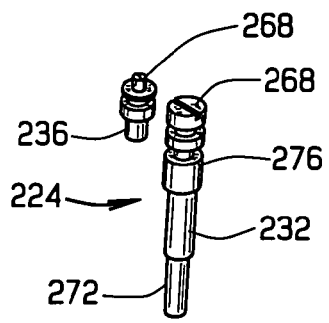
FIG. 4 is a perspective view of electrodes in accordance with one implementation of the invention.

The electrodes 224 are shown in greater detail in FIG. 4. The electrodes 224 each include a top groove 268 by which a sample is held onto the electrodes 224. A current electrode 232 includes an electrode pin 272 and an O-ring groove 276. An appropriately sized O-ring is placed in the groove 276 to form an air-tight seal between the cavity 260 in the chamber spacer 208 to prevent evolved gases from leaking to the outside environment.

Figure 5:
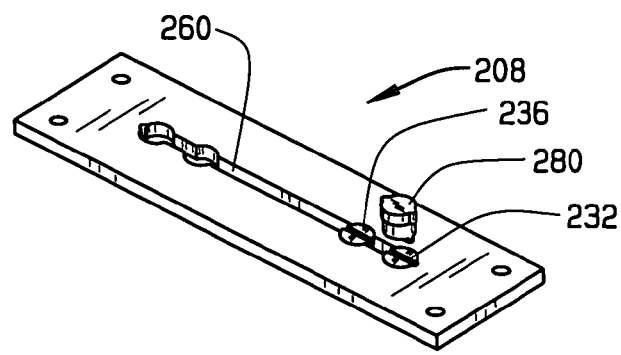
FIG. 5 is a perspective view of a chamber spacer in accordance with one implementation of the invention.
Figure 6A:
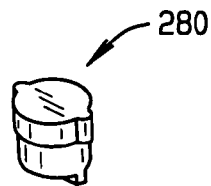
FIG. 6A is a perspective view of a compression cap in accordance with one implementation of the invention.
Figure 6B:
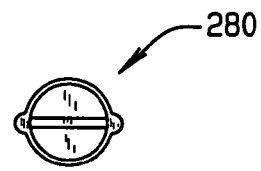
FIG. 6B is a bottom view of a compression cap in accordance with one implementation of the invention.
Figure 7A:
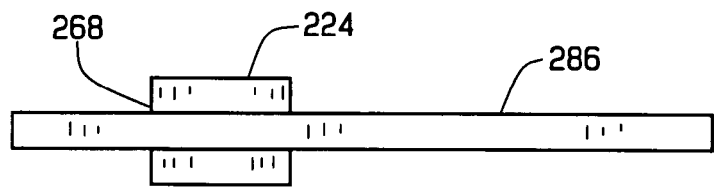
FIG. 7A is a top view of an electrode holding a sample in accordance with one implementation of the invention.
Figure 7B:
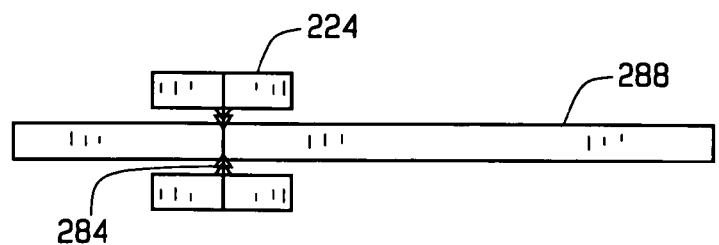
FIG. 7B is a top view of an electrode including "razor" contacts holding a sample in accordance with one implementation of the invention.

The chamber spacer 208 is shown in greater detail in FIG. 5. One current electrode 232 and one voltage sense electrode 236 are partially shown in FIG. 5 as having been inserted through the chamber spacer 208. Electrodes 224 are clamped down by compression caps 280 which are shown in greater detail in FIGS. 6A and 6B. The caps 280 are configured to force the electrode contacts into the test sample. Setscrews (not shown) in the clamp plate 220 of the top enclosure assembly 212 may be adjusted to secure a sample on the electrodes 224, to reduce contact resistance and minimize or prevent sparking during testing. The sense electrodes 236 are smaller in diameter than the current electrodes 232 to allow vapor flow around them. The electrodes 224 may be made, for example, of beryllium-copper, soft brass, or other appropriate contact material. A top view of an electrode 224 is shown in FIG. 7A. A material sample 288 is inserted in the electrode groove 268. In some configurations and as shown in FIG. 7B, the electrodes 224 include stainless steel "razor" contacts 284 that may cut into the sides of the sample material 288 to make electrical contact with the sample. The razor contacts 284 are configured to eliminate or minimize any arcing near the voltage electrodes 236.

Figure 8:
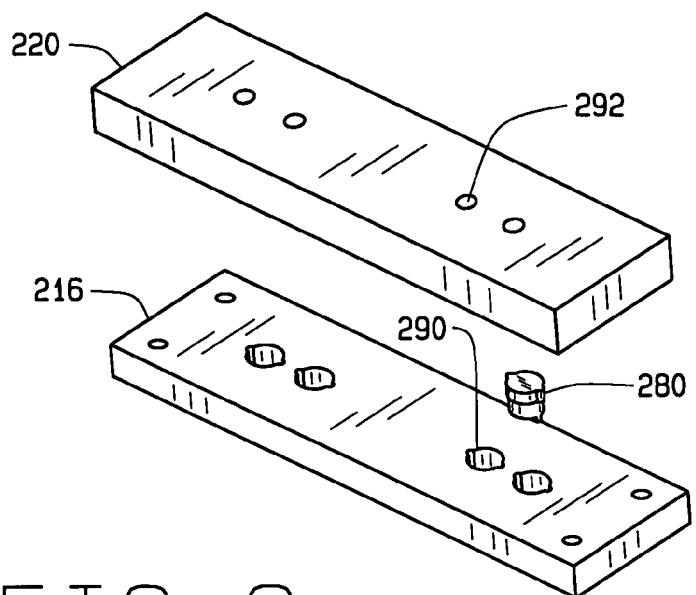
FIG. 8 is a perspective view of a cap guide plate and clamp plate in accordance with one implementation of the invention.

The cap guide plate 216 and clamp plate 220 are shown in greater detail in FIG. 8. The compression caps 280 fit into cap guide holes 290 and setscrews (not shown) in setscrew holes 292 of the clamp plate 220 may be used to adjust the contact of the sample into the sample grooves 268 of the electrodes 224. The clamp guide plate 216 and clamp plate 220 may be made of clear acrylic (e.g., Plexiglass® by Rohm & Haas Co. of Philadelphia, Pa.) to allow viewing of a sample during a test. A condensable sample collection tape may be adhered to the bottom of the clamp guide plate 216 for a test and removed thereafter.

Referring again to FIG. 3, the base plate 228 may be machined from Delrin® material. The pneumatic clamps 248 are available, for example, from Compact Automation Products LLC of Westminster, S.C. The clamps 248 may have a 25 mm bore piston that can generate approximately 70 pounds of clamp force with a 117 psi air supply. The banana jacks 244 are connected to the pulsed power supply 28. Two of the jacks 244 transmit current and two are used for voltage sensing. The chamber interlock switch 80 and arm/safe relay 84 serve to lock out a pulse discharge until the test cell 38 is clamped.

Figure 9:
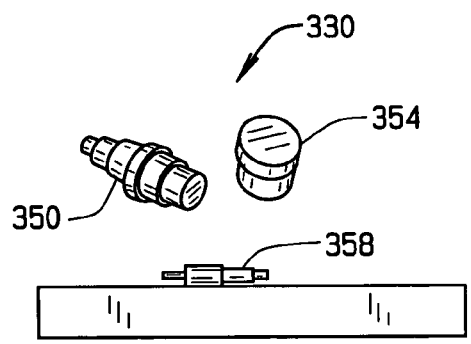
FIG. 9 is a perspective view of parts of a Schrader valve in accordance with one implementation of the invention.

The pressure transducer 40 may be removably connected to one of the valves 330 to operatively connect the pressure transducer 40 with the test chamber. The other Schrader valve 330 may be used to connect a purge gas line as further described below. Effectively a third valve may be provided by an "O" ring-sealed screw (i.e., a purge vent screw) of the pressure transducer 40. A typical Schrader valve 330 is shown in FIG. 9 in greater detail and includes a body 350, a cap 354, and a core 358. Schrader valves are commercially available and provide a small dead volume and thus good test sensitivity due to high pressure that can develop during a test. Other types of valves, however, could be used in other configurations.

When a sample has been mounted in the electrodes 224 and the test cell 38 is reassembled, the test cell is ready to be purged. To purge the chamber 36, the pressure transducer 40 is screwed onto one of the Schrader valves 330, thereby opening the valve 330. The purge vent screw is removed from the transducer 40, and a purge gas line (not shown) is attached to the other Schrader valve 330, thereby opening the other valve. A purge gas flow is started and after a few seconds it may be stopped. The purge gas line is removed, thereby closing the Schrader valve 330 to which it had been attached. The vent screw of the transducer 40 is reinserted, which seals the chamber 36 in readiness for a test.

Figure 10:
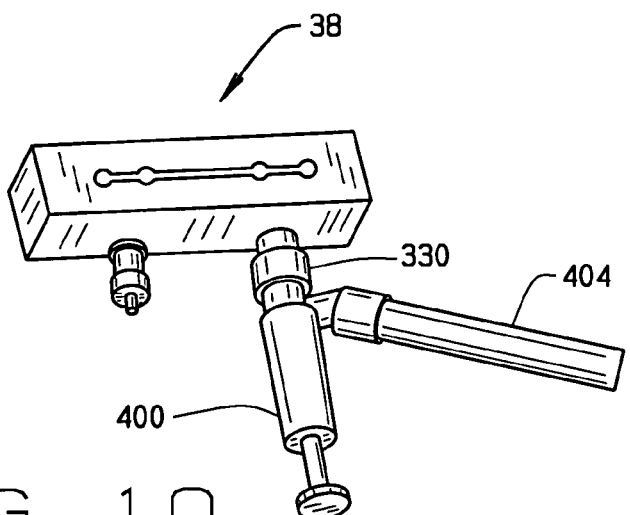
FIG. 10 is a top view of parts of a test cell and a core removal tool in accordance with one implementation of the invention.

After a test, the pressure transducer 40 is removed from the test cell 38, thereby closing the Schrader valve 330 and sealing a non-condensable volatile gas sample in the test cell 38. To extract the gas for spectroscopic analysis, a commercially available refrigeration valve core removal tool may be used. A core removal tool is indicated in FIG. 10 by reference number 400 and is attached to a Schrader valve 330 of the test cell 38. The tool 400 has a flexible pump-out line 404 connected to a spectrograph (not shown). A vacuum pump (not shown) may be used to pump down the line 404 and tool 400. A gas sample is extracted by using the tool 400 to remove the Schrader valve core 358, allowing the gas sample to transfer to the spectrograph. Condensable materials that may have volatilized during a test may be obtained for analysis by disassembling the test cell and removing an interior sample collection tape.

A pulse current measurement may be made by measuring the voltage across the shunt 64, which includes for example, five parallel 0.1-ohm, 3%, 25-watt, RLC AL, temperature compensated resistors. The voltage signal is also used in a feed back control loop that controls the test current. Test sample voltage measurements are typically made between the contacts of the sample with the voltage electrodes 236. In some implementations, an additional voltage measurement may be made between contacts of the sample with the current electrodes 232, to determine current contact resistance and how much energy is being deposited locally in the test sample at the current contacts. The pressure transducer 40 puts out a voltage signal proportional to sensed pressure. The foregoing voltage signals may be collected and recorded by the data acquisition system 32.

The data acquisition and control system 32 may include, for example, a PC-based desktop computer with a National Instruments Model N1 PCI-6052E multifunction data acquisition card. The data acquisition card may provide sixteen single-ended or eight differential, 16-bit 333 kS/s analog input channels (sample rate is divided among used channels), two 16-bit analog output channels (updateable at 333 kS/s), eight digital I/O channels and two 24-bit counters. In some implementations, three channels are used to acquire pulse data for the current, voltage and pressure waveforms at 100 kS/s, while one analog output channel provides the stimulus pulse. One additional channel may be used to monitor the capacitor bank 44 charge voltage before and after a pulse. Additionally, one digital I/O channel may be used to provide ARM/SAFE interlock control. The high voltage power supply 48 is controlled via a GPIB (general purpose interface board) interface. The high voltage power supply is less than or equal to a voltage rating for the capacitor bank 44, e.g., 450 volts.

A National Instruments LabVIEW™ application program may be used to control test parameters and capture test data for display. Test data may also be saved, for example, in an Excel formatted file for subsequent data analysis. Input parameters may include programmed current, pulse width, acquisition time and capacitor charge voltage. Output data include acquired current, voltage and pressure waveforms, calculated resistance and energy, peak pressure and total energy.

Figure 11:
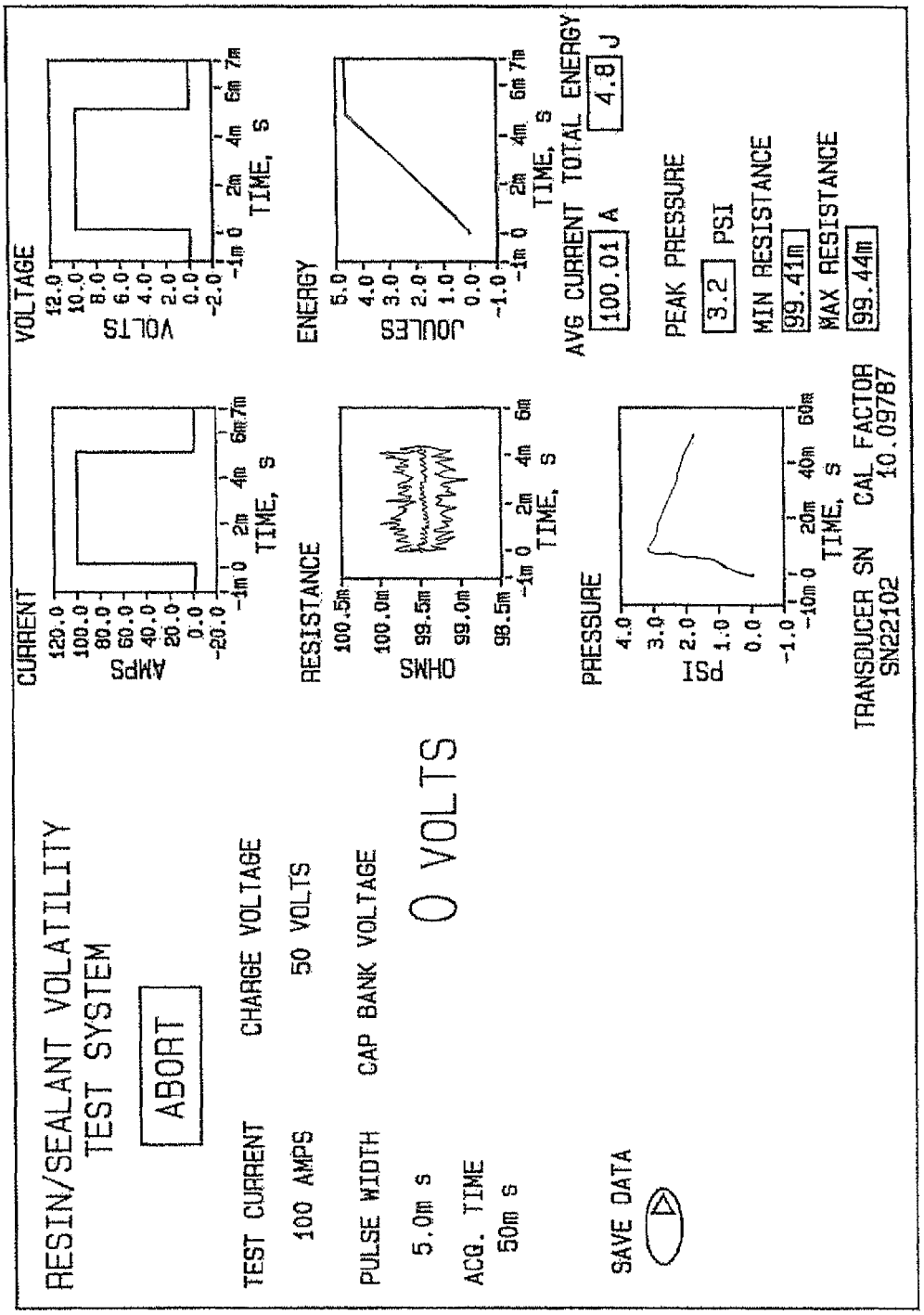
FIG. 11 is a test apparatus display screen in accordance with one implementation of the invention.

Waveform digitizing may be accomplished, for example, using a four-channel transient wave form digitizer in a computer chassis of the data acquisition system 32. Data may be transferred to the online program running in the data acquisition system 32 computer. In addition to digitized waveforms, test sample identification, test series identification, a sample initial mass and pressure transducer calibration may be input using the computer keyboard. LabVIEW™ can be used to analyze the raw data and generate a plurality of graphs and data points on a display screen. These may include current, voltage and pressure waveforms, sample temperature as a function of time during the heating pulse, the deposited energy per gram (Q/m), and the maximum pressure ($P_{max}$). An exemplary display screen is indicated generally by reference number 450 in FIG. 11.

Referring again to FIGS. 1 and 3, the acrylic guide plate 216 and clamp plate 220 on the test chamber 36 allow visual and/or video recording of a test. Slow-motion and single-frame review of the test video can provide qualitative information. For example, a single frame at the time of a heating pulse may confirm a uniform color temperature along the entire sample. Such color (when a sample is heated to sufficiently high temperature) can provide a rough indication of the sample peak temperature.

Data Analysis

A raw pressure transducer output voltage in the $i^{th}$ time interval [$P_i(V)$] may be corrected for an average pressure reading [$P_0(V)$] prior to applying a heating pulse and then divided by the pressure transducer calibration constant ($k_p$, nominally 0.1 V/psi) to obtain $P_i$(psi):

$$P_i(\text{psi})=[P_i(V)-P_0(V)]/k_p \quad (1)$$

The foregoing values may be plotted on the screen 450 and/or retained in a data file. Maximum pressure ($P_{max}$) may be extracted from the data, for example, during off-line analysis and used to characterize volatility.

Where, for example, a distance between the voltage electrodes 236 is 1.75 inches and the length of a sample is 2.94 inches, the mass $m_e$ of the sample between the voltage electrodes 236 is computed from the initial sample mass ($m_i$) as:

$$m_e=m_i(1.75/2.94)=0.595 m_i \quad (2)$$

Energy deposited in the sample between the voltage electrodes 236 as a function of time may be calculated from equation (4) using the calculated current $I(t_i)$ (equation (3)) and the measured voltage $V_v(t_i)$ across the electrodes 236. Current $I(t_i)$ may be obtained by dividing the voltage $V_R(t_i)$ across the shunt resistor(s) 64 by the resistance R:

$$I(t_i) = V_R(t_i)/R \quad (3)$$

$$Q(t_j) = \sum_{i=0}^{j} V_v(t_i)I(t_i)\Delta t \quad (4)$$

From (4) may be estimated the temperature at any time during the pulse for a composite sample as $Q/m_e$:

$$T(t_j)=112+0.496(Q(t_j)/m_e) \quad (5)$$

The foregoing is an estimate, over a range of 200-1000° C.

Q may be used to represent the total energy deposited during the heating pulse, i.e. when j is sufficiently large so that V and I have dropped back to zero. From this may be calculated the deposited energy density $Q/m_e$.

Volatility/resin performance may be evaluated by plotting Q/m versus $P_{max}$ data collected for a particular test series. The best performing materials have been observed to produce the lowest $P_{max}$ for a given Q/m. This generally is most pronounced at the higher values of Q/m.

Testing Overview

A testing procedure in accordance with one implementation shall now be described. It should be understood that various aspects of the following procedure could differ from other implementations of the invention. Tests may be run at 10-A intervals (e.g., at 20, 30, 40, 50 and 60 A.) The maximum current in amps is usually equal to the mass in mg to within the nearest 5 A. Typically it is desirable to cover a range of 100 to 1000 J/g deposited energy density with 5 or 6 spaced tests. The capacitor bank 44 is charged to 250-300 VDC. This charge voltage is set to achieve a constant current flow during pulse firing. The voltage is set at the lowest voltage of the range as possible to avoid damaging the IGBT 68 firing mechanism.

Sample Preparation

Material samples may be 0.030"±0.004" by 0.030"±0.004" in cross section. They are typically cut parallel to the fiber direction from a unidirectional laminate and are typically about 12 inches in length. Ends of the samples are typically non-uniform in thickness, so about 1 inch of one end is cut off and discarded. Cutting can be done individually with a diagonal cutter or in large quantities on a shear. Test samples are cut to a length of 2.94"±0.005". Test samples can be cut individually or as described above in mass with a shear. Test samples preferably are not used which include the last inch of the original sample (to avoid non-uniformity of ends).

Pretest Sample Installation

The test cell 38 is opened. A test sample is placed in the grooves 268 of the electrodes 224. The test cell 38 is assembled together and secured on the base 228. The caps 280 push the test sample into the grooves 268 when the lid 220 is assembled. An ohmmeter may be used to check that there is good electrical contact between the electrodes 224 and the sample (e.g., less than 10 ohms between the current electrodes 232 and similarly between the voltage electrodes 236). If resistance is higher, the cut sides of the sample may not be against the electrodes. If this is the case, the sample is reinstalled.

The screw is removed from the purge vent of the pressure transducer 40. A purge line is attached to the other Schrader valve 330 and the system is purged with dry nitrogen or other gas prior to testing. The purge line automatically opens the Schrader valve 330 when it is attached to the valve. The purge line is removed after purging. The pressure transducer 40 coaxial line is attached to the transducer and the sample is ready for testing.

Pulse Heating Test

The pulse power system 28 may be set to pre-pulse the sample (e.g., a 5-ms, 1-A pulse) and the sample may be pre-pulsed, e.g., to reduce resistance in the ends of the sample. The pulse current and duration for the test are set, and the sample is pulsed. The data acquisition system software can display and record these test parameters and responses. The online program may be run to display the maximum pressure and deposited energy (Q) on the screen. Hard copy also may be automatically and/or manually recorded. A new test sample may be mounted and the procedure may be repeated until a data set is completed.

Post Test Chemical Sample Collection

If chemical analysis is to be performed on the volatiles, the pressure transducer 40 is removed from the isolator block 204. As it is removed, the Schrader valve from which it is removed automatically closes. The test cell 38 serves as a sample container and may be removed, for example, to a lab for chemical analysis. The pressure transducer 40 and electrical connections can be disconnected while gas sample integrity is maintained.

Non-Condensable Sample Collection

The Schrader valve core removal tool is attached to one of the Schrader valves 330 on the isolation block 204 and also to a transfer line from the appropriate chemical analysis instrument (e.g., chromatography. The transfer line is evacuated. The Schrader valve core is removed. This allows the gas from the test cell to flow from the test chamber to the analysis instrument.

Condensable Sample Collection

The sample collection tape where condensable volatiles deposited during the test is removed from the clamp guide plate 216 for later chemical analysis. The tape preferably is stored in a clean sealed glass vial to prevent contamination.

For composite testing, the capacitor bank 44 is charged to 250-350 VDC dependent on the current density being tested. This charge voltage is set high enough to ensure that the capacitor bank 44 has excess energy to maintain constant current during pulse heating. The current set for composite testing may be between 20 and 70 amperes. The test cell has an internal volume of less than 0.03 cubic inch, thus allowing the evolved gases to develop pressures in the range of 2-30 psi.

Composite test sample preparation is simple and reproducible. A few plies of unidirectional laminates may be cured in an autoclave using standard composite fabrication processes. The nominal thickness of the laminate can be within 0.025 in.-0.030 in. depending on the per-ply thickness of the material, but the thickness variations within a panel should be within ±0.001 in. Test specimens may be cut from these unidirectional panels in the axial direction using a diamond saw. The final test specimens may have a dimension of 3 inches long, 0.030 inches wide and the same thickness as the fabricated panel. The sample variations within a test set may be maintained within 3% by this cutting method.

The performance of the material is evaluated based on the amount of gas generated at different specific energy (Q/m). This analysis method helps to minimize sensitivity to the weight variation between test sample sets. The gas emission is gauged by the pressure changes detected during the test. Peak pressures detected during the test generally represent a good figure of merit for the volatility performance of the materials.

Figure 12:
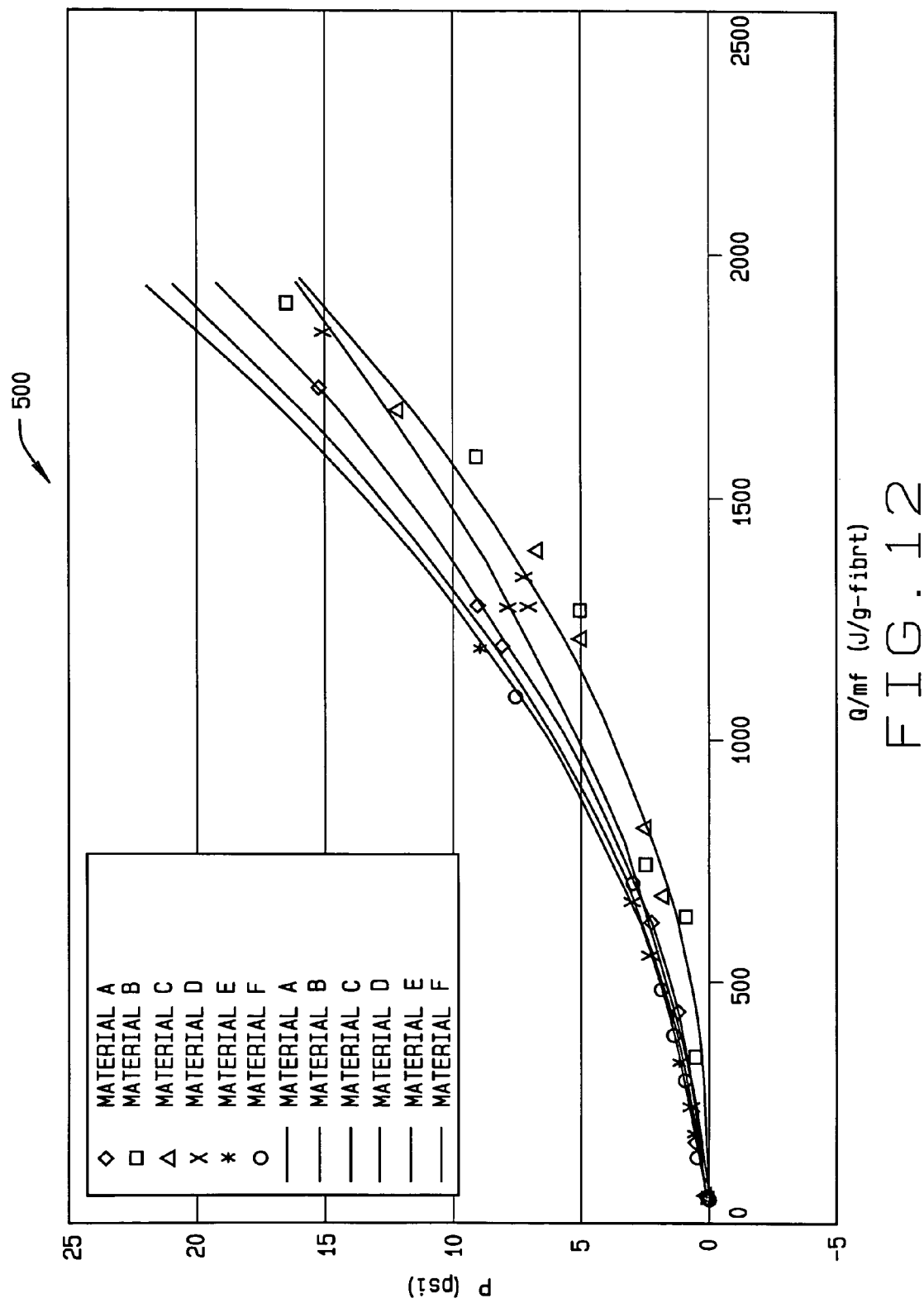
FIG. 12 is a graph indicating a volatility comparison of six materials normalized with fiber contents in accordance with one implementation of the invention.

One implementation of a method for evaluating the volatility performance of composite materials is as follows. A set of five to ten specimens from each material may be tested at different specific energies. The maximum pressures detected from each test run may be plotted against the specific energies. Each material produces a unique performance curve, and it is a signature for each material. Materials resistant to high temperatures typically have slower rise in the slope than those not resistant to high temperatures. Because specific energy is based on the total mass of the samples, resin content variation in different batch of samples may result in shifting of the performance curve. Furthermore, because the test method is based on flash heating, only thin layers of resin surrounding the carbon fibers would be heated to pyrolytic temperatures. Therefore, if the data is normalized by the energy/fiber weight ($Q/m_f$), this analysis method can yield more reproducible results regardless of the resin content variation. A graph indicating a volatility comparison of six materials normalized with fiber contents is indicated generally in FIG. 12 by reference number 500.

A prototype apparatus was built and tested in the manner previously described. This test methodology was evaluated with five different composite materials, and the results showed that the apparatus and methods described herein could be used to differentiate the volatility performance among the materials. The foregoing test method has been shown to be repeatable.

The foregoing apparatus and methods have been described in connection with testing composite materials. When composites are tested using the apparatus 20, carbon fibers in the composite materials provide heater elements to flash-heat a surrounding resin matrix. The apparatus 20 also can be used for the evaluation of fay sealant volatility. Sealant testing is different from resin volatility testing, for example, in that metal foils may be used as heater elements for flash heating of sealants.

Test specimens may be produced by casting sealants between two pieces of metal foils with a controlled thickness (e.g., 0.006 in.). This thickness is controlled within 5% in order to produce repeatable results. The samples are cut to thin strips about 0.065 inches wide and 3 inches long using a specialized cutting tool. The sealant sample mounting in the test cell may be similar to that of resin volatility tests, and also may be similar in geometry to fay sealant application geometry, for example, on fuel tanks in aircraft to simulate lightning strikes.

Two mils thick nickel or tantalum foil may be used in the samples. Nickel foil may be easier to cut and less expensive than tantalum. Because nickel has high temperature coefficient of resistance (TCR), test temperature may be determined accurately by resistance measurements of nickel foil during test runs. An actual TCR determination of the nickel foil used in the test temperature range (200-1000° C.) could serve as a calibration curve for an instrument to determine test temperatures.

Because of the high conductivity of the metal heater foils, test parameters may be set, for example, at 150 VDC and between 150-325 A. Data analysis is similar to that of resin volatility. Five to ten data points may be collected on each material at different current settings. Pressure readings (P) may be plotted against normalized specific energy (Q/mass). The resulting curve is the signature of a particular sealant in the volatility test.

The foregoing apparatus and methods provide a quick and inexpensive test to determine the volatility of material candidates when subjected to flash heating, for example, similar to a lightning strike (e.g., rapid temperature increases with rates greater than 1000 degrees C. per second). Implementations of the invention also provide a quick and inexpensive way to identify volatizeable compounds generated from the candidate materials by collecting and analyzing the volatiles evolved. Test cells can be made inexpensively, and so a plurality of test cells can be used, one test per cell, to perform series of tests. Lightning tolerance performance of downselected material candidates can then be verified using a more expensive simulated lightning test.

The foregoing apparatus and methods can also be used to evaluate the ablation characteristics of high-temperature materials when heated in a slower ramp-up rate. Implementations of the invention are less expensive and faster than existing lightning tests and provide a screening method to evaluate the volatility of resin, which is a key indicator of the tolerance of the materials to lightning strikes. Once promising materials are identified, they can then be confirmed using the more expensive traditional lightning test. The foregoing methods and apparatus can reduce the costs of material selection and provision for lightning protection and can shorten the development time and costs for new products.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method of evaluating volatility characteristics of a material, the method comprising the steps of:
   enclosing a sample of the material in a slot of a component;
   securing additional members to the component, via a plurality of external fastening elements, such that the slot forms a chamber in an airtight test cell, the airtight test cell being sealed to prevent the escape of gasses from the airtight test cell that are produced from heating of the sample of the material;
   using a pulse control electronics subsystem to deliver a pulse of current flux, having a predetermined amplitude and duration, through a probe projecting into the slot, and into the sample to simulate a lightning strike;
   measuring a pressure produced by the sample and constrained in the chamber during the pulse, the measuring performed using a pressure transducer configured to send a pressure signal from the chamber; and
   using the measured pressure to measure volatility of the material sample.

2. The method of claim 1, wherein using the measured pressure comprises:
   determining an energy deposited in the sample during the pulse; and
   relating the measured pressure to the deposited energy.

3. The method of claim 2, further comprising:
   performing the delivering, measuring and determining steps a plurality of times to obtain a plurality of measured pressures and a plurality of deposited energies; and
   relating the plurality of measured pressures to the plurality of deposited energies.

4. The method of claim 1, wherein the material sample comprises at least one of the following: a carbon fiber composite material and a sealant.

5. The method of claim 1, further comprising using fibers in the sample as heater elements to heat the sample.

6. The method of claim 1, wherein the sample is enclosed in the test cell chamber without touching ends of the test cell.

7. The method of claim 1, further comprising using a voltage between two electrodes extending through the slot and holding the sample to determine an energy deposited in the sample.

8. A method of evaluating volatility characteristics of a material, the method comprising:
   enclosing a sample of the material in a chamber of a test cell;
   delivering a pulse of current flux through the sample to simulate a lightning strike;
   measuring a pressure produced by the sample and constrained in the chamber during the pulse; and
   using the measured pressure to measure volatility of the material sample; the method further comprising curing a layer of sealant between two metal foils to form the sample.

9. A method of evaluating volatility characteristics of a material, the method comprising the steps of:
   enclosing a sample of the material in a slot of a first component;
   securing second and third components to the first component such that the components form an airtight test cell, with the slot forming an airtight chamber of the airtight test cell to prevent the escape of gasses from the airtight chamber that are produced from heating of the sample of the material;
   forming a port in the airtight test cell that is in communication with the airtight chamber;
   disposing a pressure transducer in the port such that the pressure transducer is able to sense a pressure within the airtight test cell;
   securing a pair of electrodes to the airtight test cell such that portions of the electrodes project into the chamber of without affecting the airtight condition of the chamber;
   using a pulse control electronics subsystem to deliver a pulse of current flux to at least one of the electrodes, with the pulse of current flux having a predetermined amplitude and duration, such that the current flux passes from a first one of electrodes through the sample and to a second one of the electrodes, to simulate a lightning strike impacting the sample;
   the measuring performed using a pressure transducer configured to send a pressure signal from the chamber; and
   using the measured pressure to measure volatility of the material sample.

10. A method of evaluating volatility characteristics of a material, the method comprising the steps of:
    providing a first component having a slot;
    providing a plurality of second components secured to the first component so that the components collectively form an airtight test cell, with the slot forming a chamber of the airtight test cell;
    arranging a plurality of probes to extend through at least one of the first and second components, and into the chamber;
    arranging a pressure transducer to communicate with an interior area of the chamber;
    using the probes to deliver a current pulse having a predetermined amplitude and duration into the sample to simulate a lightning strike on the sample;
    using the pressure transducer to measure a pressure within the chamber in response to the simulated lightning strike; and
    using the measured pressure to measure volatility of the sample.

* * * * *